United States Patent [19]

Mairesse et al.

[11] Patent Number: 5,582,710
[45] Date of Patent: Dec. 10, 1996

[54] ELECTROCHEMICAL CELL AND ITS USE FOR THE SEPARATION AND THE ELECTROCHEMICAL EXTRACTION OF OXYGEN

[75] Inventors: Gaetan Mairesse; Jean-Claude Boivin, both of Villeneuve d'Ascq; Gilles Lagrange, Forges les Bains; Panayotis Cocolios, Limours, all of France

[73] Assignees: L'Air Liquide, Societe Anonyme pour l'Etude et l'Exploitation des Procedes Georges Claude, Paris; Universite des Science et Technologies de Lille Cite Scientifique; Ecole Nationale Superieure de Chimie de Lille, both of Villeneuve d'Ascq, all of France

[21] Appl. No.: 244,034
[22] PCT Filed: Sep. 13, 1992
[86] PCT No.: PCT/FR93/00872
    § 371 Date: May 16, 1994
    § 102(e) Date: May 16, 1994
[87] PCT Pub. No.: WO94/06545
    PCT Pub. Date: Mar. 31, 1994

[30] Foreign Application Priority Data

Sep. 14, 1992 [FR] France .................................. 92 10904

[51] Int. Cl.⁶ .................................................. C25B 1/02
[52] U.S. Cl. ...................... 205/634; 204/421; 204/424; 204/427; 205/687; 429/33; 429/193
[58] Field of Search .................................... 204/130, 421, 204/424, 427; 429/33, 193; 205/634, 687

[56] References Cited

U.S. PATENT DOCUMENTS

| | | | |
|---|---|---|---|
| 4,725,346 | 2/1988 | Joshi | 204/242 |
| 4,789,561 | 12/1988 | Schafer et al. | 204/421 |
| 4,879,016 | 11/1989 | Joshi | 204/421 |
| 5,227,257 | 7/1993 | Abraham et al. | 429/80 |
| 5,378,345 | 1/1995 | Taylor et al. | 204/130 |

FOREIGN PATENT DOCUMENTS

| | | |
|---|---|---|
| 0239771 | 10/1987 | European Pat. Off. . |
| 0438902 | 7/1991 | European Pat. Off. . |
| 0443259 | 8/1991 | European Pat. Off. . |
| 91/01274 | 2/1991 | WIPO . |
| 91/06692 | 5/1991 | WIPO . |

*Primary Examiner*—T. Tung
*Attorney, Agent, or Firm*—Burns, Doane, Swecker & Mathis, L.L.P.

[57] ABSTRACT

The present invention relates to an electrochemical cell comprising a solid electrolyte conductive for $O^{2-}$ anions in contact with an anode and a cathode of identical or different composition, the electrolyte solid being comprised of a composition derived from $Bi_4V_2O_{11}$ of which at least one of the cationic constituent elements is substituted by at least one substituting element chosen such that the gamma phase structural type of $Bi_4V_2O_{11}$ is maintained, as well as the equilibrium of charges, at least one of the anode or the cathode including two parts, a first part being of a mixed electronic and ionic conductive material in contact with the solid electrolyte, the second part being an electronic conductive material superposed on the first part. The invention equally relates to the use of the electrochemical cell with a view towards the separation or the extraction of oxygen.

22 Claims, No Drawings

ELECTROCHEMICAL CELL AND ITS USE FOR THE SEPARATION AND THE ELECTROCHEMICAL EXTRACTION OF OXYGEN

The present invention has for its object an electrochemical cell comprised of a solid electrolyte, an anode and a cathode as well the use of this electrochemical cell with a view towards the electrochemical separation of gases from a mixture of at least one gas and of oxygen or with a view towards the extraction of oxygen from a molecule containing oxygen.

It is known that some solid electrolytes, classically comprising, for example, compositions derived from oxides of zirconium, yttrium, bismuth or cerium, containing or not containing dopants such as ytterbium or calcium, can be used as conductors of $O^{2-}$ ions, when they are subject to an electric field and/or a difference of partial pressure of oxygen. These solid electrolytes typically possess the same base structure, derived from the so-called structure of fluorine type possessing oxygenated gaps. They permit a conduction of $O^{2-}$ ions which is essentially tri-dimensional.

Besides, solid electrolyte conductors for $O^{2-}$ ions have been described in patent application WO91/01274 the teachings of which are totally incorporated herein by reference. These electrolytes are comprised of a composition derived from $Bi_4V_2O_{11}$ and of which at least one of the constituent elements is substituted by one or several substituting elements chosen of the kind such that the structural type of the gamma phase of $Bi_4V_2O_{11}$ is maintained, as well as the equilibrium of the charges. This type of solid electrolyte presents a lamellar structure in which the mechanism of conduction of the ions $O^{2-}$ is essentially bi-dimensional.

Thus, the solid electrolytes comprised of a composition derived from $Bi_4V_2O_{11}$ can be distinguished from classical solid electrolytes, by their chemical composition, their crystalline structure and their mode of conduction of $O^{2-}$ ions.

Some solid electrolytes comprised of compositions derived from $Bi_4V_2O_{11}$ possess the remarkable property of permitting an anionic conductivity of $10^{-3}\psi^{-1}cm^{-1}$ at 200° C., which is of the order of one hundred times superior to the performances of materials currently on the market. Such classical materials are even inoperative at temperatures less than 300° C. In order to attain an anionic conductivity of the order of $10^{-3}\psi^{-1}cm^{-1}$, it is necessary to take them to temperatures greater than about 600° C.

It, however, has been observed by the Applicants that classical electrodes, essentially based on silver or gold, deposit, for example, under the form of a lacquer on the solid electrolyte, lead, when they are associated with a solid electrolyte comprised of a composition derived from $Bi_4V_2O_{11}$, to a rapid deactivation of the electrochemical cell. Such a deactivation is not produced when the solid electrolyte is comprised, for example, of a classical stabilized zirconium. It is well understood that such a deactivation of the electrochemical cell is not compatible with exploitation on an industrial scale. Without being bound to a theoretical explanation, the Applicants were able to attribute the deactivation to a chemical reaction between one or several of the constituent elements of the electrolyte derived from $Bi_4V_2O_{11}$ and of the electrode based on silver. In the case of gold, its diffusion in the electrolytic material often leads to a very strong increase in the surface resistivity, which is prejudicial to good distribution of the density of the current, being capable of leading to the phenomena of craterization which leads to the deterioration of the cell.

The Applicants pursued their research and have developed an electrochemical cell whose solid electrolyte is comprised of a composition derived from $Bi_4V_2O_{11}$ and is not rapidly deactivated. An object of the present invention thus consists of an electrochemical cell comprised of such a solid electrolyte, an anode and a cathode permitting use over long duration, even on an industrial scale, notably with a view towards the electrochemical separation of oxygen from a mixture of gas containing oxygen or with a view towards the electrochemical extraction of oxygen from a molecule containing oxygen.

The present invention thus relates to an apparatus comprising a solid electrolyte conductor of $O^{2-}$ anions in contact with an anode and a cathode of identical or different composition, such solid electrolyte being comprised of a composition derived from $Bi_4V_2O_{11}$ of which at least one of the constituent cationic elements is substituted by at least one substitution element chosen of the kind such that the gamma phase structural type of $Bi_4V_2O_{11}$ is maintained as well as the equilibrium of the charges, said apparatus being characterized in that at least one of the anode or of the cathode includes two parts, a first part being of a mixed electronic and ionic conductor material in contact with the solid electrolyte, the second part being of an electronic conductive material which superposes the first part.

Preferably the anode and the cathode each include said two parts.

Said mixed electronic and ionic conductive material can be a ceramic such as manganites, colbaltites or ferrites of lanthanum doped with strontium, cerium, or thorium, the compounds of formula (I):

$$YBa_2Cu_3O_{7-x} \qquad (I)$$

where x ranges between 0 and 1, the oxides of bismuth or the oxides of cerium doped by one or two cations, the oxides of vanadium and strontium, the oxides of vanadium and lead, the oxides of calcium and titanium of formula (II):

$$CaTi_{1-x'}M^1_{x'}O_{3-t} \qquad (II)$$

where $M^1$ is a transition element and x' and t have limited values which are a function of the nature of $M^1$.

Preferably the mixed electronic and ionic conductive material is a manganite of lanthanum doped with strontium (LSM), a formula (III):

$$La_{1-x''}Sr_{x''}MnO_3 \qquad (III)$$

where x" ranges strictly between 0 and 1.

The electronic conductor material can comprise an element in metallic state, an alloy containing at least one element in metallic state or a material containing at least one element in cationic state.

Preferably, the material containing at least one element in cationic state is an oxide of one or several elements in cationic state, and more preferably, an oxide of a single element in cationic state.

Preferably, the electronic conductive material is a material which is essentially or uniquely an electronic conductive material.

The constituent element of the electronic conductive material can advantageously be a transition metal, such as the lanthanides and actinides such as lanthanum, cerium, ytterbium or niobium or a metal of groups $III_b$, $IV_b$, $V_b$, $VI_b$, or $VII_b$ of the Periodic Table.

In a still more advantageous manner, said metal is chosen from among iron, cobalt, nickel, copper, zinc and gold.

Typically, the solid electrolyte comprises a composition derived from $Bi_4V_2O_{11}$ corresponding to the formula (IV):

$$(Bi_{2-w} M_w O_2)(V_{1-y} M'_y O_z) \quad (IV)$$

in which:

M represents one or several substitution elements of Bi, chosen from among those having an oxidation number less than or equal to 3.

M' represents one or several substitution elements of V, chosen from among those having any oxidation number, the limit on the values of w, y and therefore z being a function of the nature of the substituting elements M and M'.

A particularly preferred family of the composition derived from $Bi_4V_2O_{11}$ according to the present invention consists of compositions in which only the vanadium atom is partially substituted by one or several elements. These compositions correspond to the formula (V):

$$(Bi_2O_2)(V_{1-y} M'_y O_z) \quad (V)$$

in which M' is as defined above, y not being zero.

M' is advantageously selected from among the alkaline metals, alkaline earth metals, transition metals, notably the metals of groups III to V of the Periodic Table and the rare earths.

Preferably, M' is chosen among zinc, copper, nickel, cobalt, iron, manganese and cadmium.

The solid electrolyte can also be comprised of a composition derived from $Bi_4V_2O_{11}$ where only the bismuth atom is partially substituted by one or several elements. Such a composition corresponds to the formula (VI):

$$(Bi_{2-w} M_w O_2)(VO_z) \quad (VI)$$

in which M and z are such as defined above and w not being zero. Preferably, M is a rare earth, such as lanthanum.

The solid electrolyte again can be comprised of a composition derived from $Bi_4V_2O_{11}$ of formula (IV) such as defined above, in which w and y are not zero.

The compositions derived from $Bi_4V_2O_{11}$ such as described above, can be prepared according to the process described in patent application WO 91/01274.

These compositions generally being in the form of a powder are advantageously put in form for use as solid electrolytes in the apparatus according to the invention.

Thus, the solid electrolyte may or may not be present in the form of a supported tube by a porous support such as a tube of a ceramic such as alumina, a porous metal or a manganite of lanthanum doped with strontium (LSM), of a disc, a plate or of a multi-layer aveole. The thickness of the solid electrolyte can range between 0.001 and 2 mm and preferably between 0.01 and 1 mm. The anode and the cathode are generally disposed on two opposite faces of the solid electrolyte.

The placement into contact of the anode and/or the cathode according to the invention with solid electrolyte can be carded out according to varying techniques. The first part, a mixed electronic and ionic conductive material, notably when it is present as an underlayer, can be deposited on the surface of the electrolyte by methods such as the application of a layer of paint by means of a brush, silkscreen painting, soaking, aerosol projection, plasma aerosol projection, chemical deposition at vapor state (CVD), deposition under a vacuum (PVD) including evaporation under vacuum and sputtering, chemical deposition solution without employing an electrical current, chemical deposition in solution under the influence of a difference in potential. According to the method chosen, said material can be present in admixture with different excipients such as solvents or binders chosen of the type which are easily eliminated from the surface of the solid electrolyte. Thus, if the chosen method is the application by painting, said constituent material of the underlayer is mixed with solvents and organic binders which can be eliminated by an appropriate thermal treatment.

According to the chosen method, said material following its deposit on the electrolyte can be sintered at temperatures which can range between 20° and 850° C.

The second part of the anode and/or of the cathode can be superposed on the first part by employing one of the methods described above. This method can be identical or different from that employed for the application of the first part.

As indicated with respect to the first part and according to the method of depositing the second part, it can be subsequently sintered at temperatures which can range between 20° and 850° C.

The invention relates equally to the use of the electrochemical cell described above for the construction of oxygen gauges, of amperometric meters of combustible batteries, and of installations for the electrochemical separation of gas, notably oxygen, from a mixture of gas containing oxygen or for an installation for the electrochemical extraction of oxygen from a molecule containing oxygen.

With respect to the installation for the electrochemical separation of oxygen from a mixture of gas containing oxygen, in which the electrochemical cell of the invention can be employed, there can be cited the work described in Solid State Ionics 28–30 (1988) 524–528 by Dumelié M. et al.

In this type of installation, the apparatus according to the invention notably permits separation of oxygen, from air, or from another mixture of nitrogen and oxygen or from a mixture of argon and oxygen.

With respect to the installations for the electrochemical extraction of oxygen from a molecule containing oxygen, there can be cited those described in the Japanese patent applications 85/172360 and 85/172359.

In this type of installation, the electrochemical cell according to the invention permits extraction of oxygen from carbon monoxide or from carbon dioxide. Installations of the same type permit the use of the electrochemical cell according to the invention for extracting oxygen from water, from $NO_x$ or $SO_x$.

The examples which follow have for their object the illustration of the present invention.

EXAMPLE 1

(According to the Invention)

There is described an installation for the electrochemical separation of oxygen from air in the following manner:

1) There is prepared a solid electrolyte in the form of a disc starting from a powder of a composition derived from $Bi_4V_2O_{11}$ of formula $Bi_2V_{0.9}Cu_{0.1}O_{5.35}$ (Bi Cu $VO_x$). To do this, the powder is ground in a manner so as to obtain grains having an average diameter of about 6 microns, the granulometry varying from 0.3 to 15 microns. The disc is obtained by pressing by applying to the ground powder a force on the order of 6 tons. Such presents a surface of 2 cm² and a thickness of 1.2 mm.

2) The disc is then sintered for five hours in an air atmosphere in such a manner so as to obtain a mechanically resistant product impermeable to gases.

3) On a part of each of the surfaces of the discs, there is deposited with the aid of a brush, an underlayer of a lacquer having a base of lanthanum manganite doped with strontium of the formula $La_{0.5}Sr_{0.5}MnO_3$ (LSM).

The disc is dried at 150° C. in order to eliminate solvents and binders of the lacquer, then the layers of LSM are sintered at 850° C. for about 6 hours in an air atmosphere.

4) On each of the underlayers of LSM, there is applied by brush an ink of gold base. It is dried for an hour at 150° C. and the solvents and organic binders are eliminated by bringing the temperature to 350° C. for still another hour. Then the disc is baked at 600° C. for about one minute.

5) The disc of solid electrolyte provided on each of its surfaces with an electrode forms of a cell which is deposited on the section of a stainless steel conductor tube. In order to maintain in a stable manner the disc on the section of the stainless steel tube, there is applied an adhesive cement impermeable to gas and electrically isolated on the section of the disc and on an external part of said tube. The electric contact on the anodic side is comprised of the stainless steel tube and the electric contact on the cathode side of is assured by an external metallic rod of which one of the extremities is in contact with the gold superposing the LSM.

In functioning for the electrochemical separation of oxygen from air, the cathodic side of the disc is placed in contact with air. The pure oxygen is recovered in the stainless steel tube, from the anodic side of the cell.

The stainless steel tube and the metallic rod are linked to a generator. The cell is subjected to a temperature of 300° C. The applied intensity to the terminals of the cell is 0.3 A, which corresponds to a potential on the order of 9.5 to 12.4 volts for the duration of the experiment. The cell, therefore, functioned under a current density of 1493 A/m$^2$.

The production of pure oxygen was from 0.25 ml/min brought back to unity at the surface (1 cm$^2$) for a duration of 8 days.

EXAMPLE 2

(Comparative)

There is prepared a installation following the stages 1–5 of Example 1, but omitting, however, stage 4. The anode and the cathode of the cell are, therefore, uniquely comprised of a layer of LSM.

With a view towards the production of pure oxygen starting from air, the installation is subjected to a temperature of 480° C. and there is applied an intensity of 0.3 A to the terminals of the cell. This intensity corresponds to a potential of 1 to 6 volts for the duration of the experiment. This cell, therefore, functioned under a current density of 1493 A/m$^2$.

The production of pure oxygen under these conditions was from 0.01 ml/min brought back to unity at the surface (1 cm$^2$) for a duration of 20 minutes after which all production of oxygen had ceased.

EXAMPLE 3

(Comparative)

There is described an installation similar to that of Example 1 but the disc had a surface of 2.2 cm$^2$ and the cathode and the anode are comprised of a layer of gold in direct contact with the surfaces of the solid electrolytic.

With view towards the production of pure oxygen starting from air, the cell is subjected to a temperature of 286° C. The applied intensity to the terminals of the cell is 0.3 A. This intensity corresponds to a potential of 14 volts. This cell, therefore, functioned under a current density of 1493 A/m$^2$.

The production of pure oxygen in these conditions was 0.21 ml/min, brought back to unity of the surface (1 cm$^2$) for a duration of 345 minutes, after which all production of oxygen had ceased and the gold had disappeared from the surface of the solid electrolyte.

EXAMPLE 4

(Comparative)

There is described an installation similar to that of Example 3, but where the disc of the cell has a surface of 2.27 cm$^2$, a thickness of 1.1 mm, and where the anode and the cathode are silver instead of gold. The silver is likewise deposited on the electrolyte by the application by brush of ink, this time of silver base.

With a view towards the production of pure oxygen starting from air, the cell is subjected to a temperature of 420° C.

The applied intensity to the terminals of the cell is 0.3 A. This intensity corresponds to a potential of 11 v. This cell, therefore, functioned under a current density of 1322 A/m$^2$. The production of pure oxygen in these conditions was 0.01 ml/mm brought back to unity of the surface (1 cm$^2$) for a duration of 10 min. During this very short delay of functioning, the silver of the electrodes had apparently reacted with the electrolyte to form a material of different aspect from that of the start and inactive for the separation of oxygen from air.

We claim:

1. Electrochemical cell comprising:

a solid electrolyte conductive for O$^{2-}$ anions comprising a composition wherein at least one of Bi and V is substituted in part by at least one substituting element which maintains gamma structural phase and charge equilibrium of said Bi$_4$V$_2$O$_{11}$;

an anode and a cathode of identical or different composition in contact with said solid electrolyte, wherein at least one of the anode and the cathode includes first and second parts, the first part being of a ceramic mixed electronic and ionic conductive material In contact with the solid electrolyte and the second part being of an electronic conductive material and superposed on the first part wherein said anode and cathode do not lead to a rapid deactivation of the electrochemical cell.

2. Electrochemical cell according to claim; wherein said first part forms an under-layer covered with a layer of said second part.

3. Electrochemical cell according to claim 1 wherein the mixed electronic and ionic conductive material is a ceramic selected from the group consisting of (a) manganites, colbaltites, or ferrites of lanthanum doped with strontium, cerium, or thorium, (b) compounds of formula (I):

$$YBa_2Cu_3O_{7-x} \qquad (I)$$

where x ranges between 0 and 1, (c) oxides of bismuth or oxides of cerium doped by one or two cations, (d) oxides of vanadium and strontium, (e) oxides of vanadium and lead, and (f) oxides of calcium and titanium of formula (II):

$$CaTi_{1-x'}M^1_{x'}O_{3-t} \qquad (II)$$

where $M^1$ is a transition metal and x' and t have limited values which are a function of the nature of $M_1$.

4. Electrochemical cell according to claim 3 wherein said ceramic is a managanite of lanthanum doped with strontium of the formula (III):

$$La_{1-x''}Sr_{x''}MnO_3 \qquad (III)$$

where x" ranges strictly between 0 and 1.

5. Electrochemical cell according to claim 1 wherein the electronic conductive material comprises an element in metallic state, an alloy including at least one element in a metallic state or a material including at least one element in cationic state.

6. Electrochemical cell according to claim 5 wherein the electronic conductor material is an oxide of at least one element in a cationic state.

7. Electrochemical cell according to claim 6 wherein the electronic conductor material is an oxide of a single element in cationic state.

8. Electrochemical cell according to claim 5 wherein said element is a transition metal.

9. Electrochemical cell according to claim 8 wherein said element is iron, cobalt, nickel, copper, zinc or gold.

10. Electrochemical cell according to claim 1 wherein the composition corresponds to the formula (IV):

$$(Bi_{2-w}M_wO_2)(V_{1-y}M'_yO_z) \qquad (IV)$$

in which:

M represents one or several elements of substitution of Bi, chosen from among those having an oxidation number less than or equal to 3, M' represents one or several substitution elements of V w, y and z are a function of the nature of the substituting elements M and M'.

11. Electrochemical cell according to claim 10 wherein w and y in the formula (IV). are not zero.

12. Electrochemical cell according to claim 1 wherein the composition corresponds to the formula (V):

$$(Bi_2O_2)(V_{1-y}M'_yO_z) \qquad (V)$$

in which:

M' is one or several substitution elements of V, and y is not equal to zero.

13. Electrochemical cell according to claim 12 wherein M' is an alkaline metal, an alkaline earth metal, a transition metal or a rare earth.

14. Electrochemical cell according to claim 13 wherein M' is a transition metal from groups III to V of the Periodic Table.

15. Electrochemical cell according to claim 13 wherein the composition corresponds to the formula (VI):

$$(Bi_{2-w}M_wO_2)(VO_z) \qquad (VI)$$

in which M and z are as defined in claim 8, w not being zero.

16. Electrochemical cell according to claim 15 wherein is a rare earth.

17. Electrochemical cell according to claim 16 wherein said rare earth is lanthanum.

18. Method for electrochemical separation of oxygen from a gaseous admixture containing oxygen comprising contacting said gaseous admixture with the electrochemical cell according to claim 1 and recovering oxygen from said cell.

19. Method according to claim 18 wherein said gaseous admixture containing oxygen is a mixture of nitrogen and oxygen or a mixture of argon and oxygen.

20. Method according to claim 18 wherein said gaseous admixture is air.

21. Method for electrochemical extraction of oxygen from a molecule including oxygen comprising contacting said molecule with the electrochemical cell according to claim 1 and separating oxygen from said molecule.

22. Method according to claim 21 wherein said molecule including oxygen is water, carbon dioxide, carbon monoxide, $NO_x$ or $SO_x$.

* * * * *

UNITED STATES PATENT AND TRADEMARK OFFICE
CERTIFICATE OF CORRECTION

PATENT NO. : 5,582,710
DATED : December 10, 1996
INVENTOR(S) : Gaetan Mairesse, et al.

It is certified that error appears in the above-indentified patent and that said Letters Patent is hereby corrected as shown below:

Title page,

Item [22] please delete the date "September 13, 1992", and insert therefore --September 13, 1993--.

Signed and Sealed this

Eighth Day of April, 1997

Attest:

BRUCE LEHMAN

*Attesting Officer*      *Commissioner of Patents and Trademarks*